United States Patent
Hoshi et al.

Patent Number: 5,681,979
Date of Patent: Oct. 28, 1997

[54] PROCESS FOR THE PRODUCING OF ALKYLCYCLOPENTANONE DERIVATIVES

[75] Inventors: Hajime Hoshi; Satoru Kumazawa, both of Iwaki, Japan

[73] Assignee: Kureha Kagaku Kogyo Kabushiki Kaisha, Japan

[21] Appl. No.: 609,374

[22] Filed: Mar. 1, 1996

[30] Foreign Application Priority Data

Mar. 10, 1995 [JP] Japan .................. 7-078365

[51] Int. Cl.⁶ .................................. C07C 69/76
[52] U.S. Cl. ........................................ 560/51
[58] Field of Search ............................ 560/51

[56] References Cited

FOREIGN PATENT DOCUMENTS 0 267 778  5/1988  European Pat. Off. .
731083  11/1996  European Pat. Off. .

*Primary Examiner*—Paul J. Killos
*Attorney, Agent, or Firm*—Parkhurst, Wendel & Burr, L.L.P.

[57] ABSTRACT

The present invention provides a process for producing alkylcyclopentanone derivatives of formula (1) by reacting alkyl cyclopentanone derivatives of formula (2) and alkyl halides of formula (3) in an organic solvent in the presence of molecular sieves and an alkaline metal hydroxide:

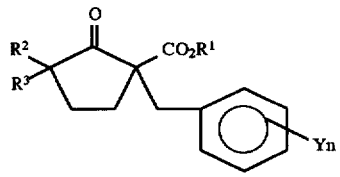

(1)

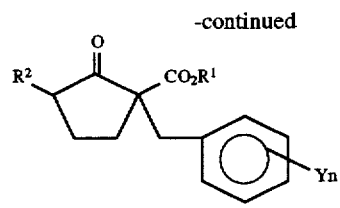

(2)

$R^3X$  (3)

wherein $R^1$ is $C_1$–$C_4$ alkyl group; $R^2$ is hydrogen atom or $C_1$–$C_5$ alkyl group; $R^3$ is $C_1$–$C_5$ alkyl group; Y is halogen atom, $C_1$–$C_5$ alkyl group, $C_1$–$C_5$ haloalkyl group, phenyl group, cyano group or nitro group; n is an integer from 0 to 5; when n is 2 or greater, Y's may be identical or different; $R^3$ in formula (3) is the same as $R^3$ in formula (1); and a process for preparing alkylcyclopentanone derivatives of formula (5) by reacting cyclopentanone derivatives of formula (4) and alkyl halides of formula (6) in an organic solvent in the presence of molecular sieves and an alkaline metal hydroxide:

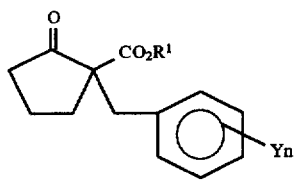

(4)

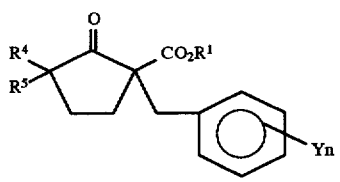

(5)

$R^kX$  (6)

wherein $R^1$ is $C_1$–$C_4$ alkyl group; $R^4$ is hydrogen atom or $C_1$–$C_5$ alkyl group; $R^5$ is $C_1$–$C_5$ alkyl group; $R^k$ is either $R^4$ or $R^5$; Y is halogen atom, $C_1$–$C_5$ alkyl group, $C_1$–$C_5$ haloalkyl group, phenyl group, cyano group or nitro group; n is an integer from 0 to 5; when n is 2 or greater, Y's may be identical or different.

20 Claims, No Drawings

PROCESS FOR THE PRODUCING OF ALKYLCYCLOPENTANONE DERIVATIVES

BACKGROUND OF THE INVENTION

The present invention relates to a process for producing alkylcyclopentanone derivatives which are useful compounds as an intermediate for the preparation of bactericidal azole derivatives.

The alkylcyclopentanone derivatives which can be produced according to the process of the present invention are the 2-oxocyclopentanecarboxylic acid esters alkylated at the 3-position of cyclopentane ring and are known as useful compounds which is able to derive to an intermediate for the preparation of fungicidal azole derivatives (U.S. Pat. Nos. 4,938,792 and 5,414,105).

U.S. Pat. Nos. 4,938,792 and 5,414,105 disclose processes for preparing dialkyl-2-oxocyclopentanecarboxylic acid alkyl esters by reacting 2-oxocyclopentanecarboxylic acid alkyl esters and alkyl halides in a solvent such as benzene or tetrahydrofuran in the presence of a base.

The above U.S. Pat. Nos. 4,938,792 and 5,414,105 describe that alkylcyclopentanone derivatives usable as the said intermediate can be obtained by reacting 1-(4-chlorobenzyl)-2-oxocyclopentanecarboxylic acid methyl ester and alkyl halides in the presence of a base such as alkaline metal hydrides, alkaline metal carbonates, alkaline metal hydroxides, alkaline metal alkoxides, alkyl alkaline metals and the like. U.S. Pat. Nos. 4,958,792 and 5,414,105 teach that the objective alkylcyclopentanone derivatives can be produced in a high yield particularly when an alkaline metal hydride is used as base.

In this method, however, since hydrogen is produced in the course of reaction because of use of sodium hydride, special care must be taken in the process and also the preparation equipment is complicated.

Among the bases usable in the above process, alkaline metal hydroxides such as sodium hydroxide and potassium hydroxide are the most inexpensive and easy to handle. Use of such inexpensive alkaline metal hydroxides is desirable especially for the commercial production of the objective compound. However, when an alkaline metal hydroxide is used as base, the reaction activity becomes lower than that of when an alkaline metal hydride is used as base.

It has been therefore a technical problem to be solved to provide a process which enables the high-yield preparation of alkylcyclopentanone derivatives of the following formula (1) by alkylating the 3-position of the cyclopentane ring using an alkaline metal hydroxide as base which is easy to handle:

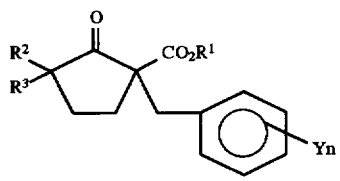
(1)

wherein $R^1$ is $C_1$–$C_4$ alkyl group; $R^2$ is hydrogen atom or $C_1$–$C_5$ alkyl group; $R^3$ is $C_1$–$C_5$ alkyl group; Y is halogen atom, $C_1$–$C_5$ alkyl group, $C_1$–$C_5$ haloalkyl group, phenyl group, cyano group or nitro group; n is an integer from 0 to 5; when n is 2 or greater, Y's may be identical or different.

As a result of the present inventors' studies for accomplishing the above theme, it has been found that by reacting a cyclopentanone derivative represented by the following formula (2) or (4) and an alkyl halide represented by the following formula (3) or (6) in an organic solvent in the presence of an alkaline metal hydroxide and molecular sieves, the objective product alkylcyclopentanone derivative represented by the above-shown formula (1) or the following formula (5) can be obtained in a higher yield than that of when the above alkylation is carried out using an alkaline metal hydroxide alone, and that particularly when using a 2-oxocyclopentanecarboxylic acid alkyl ester in which the alkyl group of the ester moiety has a branched structure, the effect of molecular sieves is further enhanced to allow an obtaining of the objective product in a still higher yield. The present invention has been attained on the basis of the above finding.

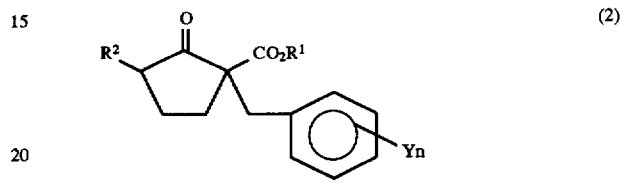
(2)

wherein $R^1$ is $C_1$–$C_4$ alkyl group; $R^2$ is hydrogen atom or $C_1$–$C_5$ alkyl group; Y is halogen atom, $C_1$–$C_5$ alkyl group, $C_1$–$C_5$ haloalkyl group, phenyl group, cyano group or nitro group; n is an integer from 0 to 5; when n is 2 or greater, Y's may be identical or different.

(3)

wherein $R^3$ is the same as $R^3$ in formula (1).

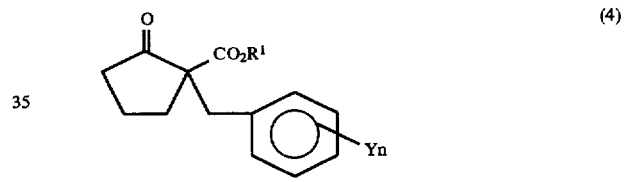
(4)

wherein $R^1$ is $C_1$–$C_4$ alkyl group; Y is halogen atom, $C_1$–$C_5$ alkyl group, $C_1$–$C_5$ haloalkyl group, phenyl group, cyano group or nitro group; n is an integer from 0 to 5; when n is 2 or greater, Y's may be identical or different.

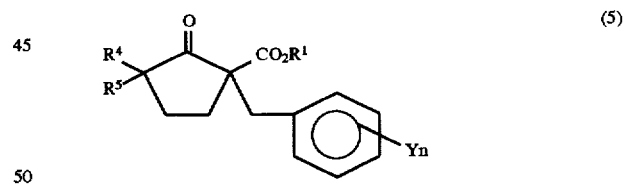
(5)

wherein $R^1$ is $C_1$–$C_4$ alkyl group; $R^4$ is $C_1$–$C_5$ alkyl group; $R^5$ is $C_1$–$C_5$ alkyl group; Y is halogen atom, $C_1$–$C_5$ alkyl group, $C_1$–$C_5$ haloalkyl group, phenyl group, cyano group or nitro group; n is an integer from 0 to 5; when n is 2 or greater, Y's may be identical or different.

(6)

wherein $R^k$ represents either $R^4$ or $R^5$ which are the same as $R^4$ and $R^5$ in formula (5).

SUMMARY OF THE INVENTION

In aspects of the present invention, there are provided a process for producing alkylcyclopentanone derivatives of the formula (1) by reacting cyclopentanone derivatives of the formula (2) and alkyl halides of the formula (3) in the presence of molecular sieves and an alkaline metal hydroxide (Reaction scheme 1):

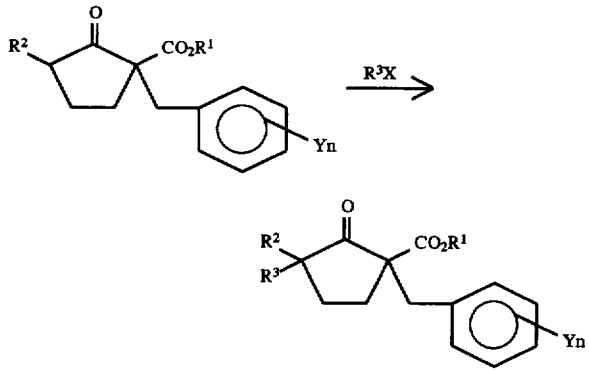

wherein $R^1$ is $C_1$–$C_4$ alkyl group; $R^2$ is hydrogen atom or $C_1$–$C_5$ alkyl group; $R^3$ is $C_1$–$C_5$ alkyl group; Y is halogen atom, $C_1$–$C_5$ alkyl group, $C_1$–$C_5$ haloalkyl group; phenyl group, cyano group or nitro group; n is an integer from 0 to 5; when n is 2 or greater, Y's may be identical or different; and a process for producing alkylcyclopentanone derivatives of the formula (5) by reacting cyclopentanone derivatives of the formula (4) and alkyl halides of the formula (6) in the presence of molecular sieves and an alkaline metal hydroxide (Reaction scheme 2):

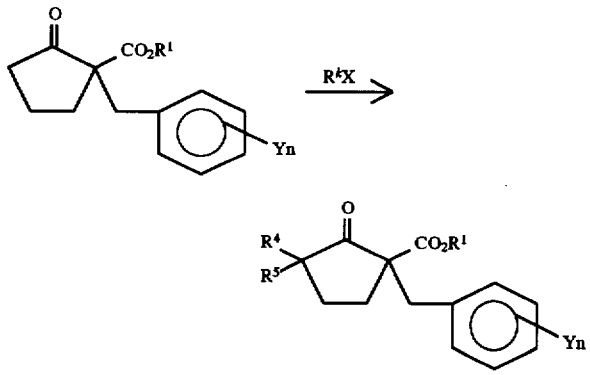

wherein $R^1$ is $C_1$–$C_4$ alkyl group; $R^4$ is hydrogen atom or $C_1$–$C_5$ alkyl group; $R^5$ is $C_1$–$C_5$ alkyl group; $R^k$ is either $R^4$ or $R^5$; Y is halogen atom, $C_1$–$C_5$ alkyl group, $C_1$–$C_5$ haloalkyl group, phenyl group, cyano group or nitro group; n is an integer from 0 to 5; when n is 2 or greater, Y's may be identical or different.

DETAILED DESCRIPTION OF THE INVENTION

The substitution of the hydrogen atom at the 3-position of cyclopentane ring with an alkyl halide includes the following three cases:

(11) One hydrogen atom is electrophilically substituted.

(12) Two hydrogen atoms are electrophilically substituted with a same alkyl group.

(13) Two hydrogen atoms are electrophilically substituted with different alkyl groups.

In either case, when the reaction is carried out with an alkaline metal hydroxide as base in the presence of molecular sieves, the objective product can be obtained in a higher yield than that of when the reaction is carried out with an alkaline metal hydroxide alone.

The effect of the molecular sieves is particularly remarkable when $R^1$ in the ester moiety of the compound of formula (2) or (4) is a branched alkyl group.

Preferred examples of substituents in the definition of the alkylcyclopentanone derivatives of formula (1) or (5) which is obtained in the present invention are shown below:

$C_1$–$C_4$ alkyl groups represented by $R^1$: methyl, ethyl, 1-methylethyl, propyl, 1-methylpropyl, butyl and 1,1-dimethylethyl group.

$C_1$–$C_5$ alkyl groups represented by $R^2$–$R^5$: methyl, ethyl, 1-methylethyl, propyl, 2-methylpropyl, butyl, 3-methylbutyl and pentyl group.

Halogen atoms represented by Y: fluorine atom, chlorine atom and bromine atom.

$C_1$–$C_5$ alkyl groups represented by Y: methyl, ethyl, 1-methylethyl, propyl, 2-methylpropyl, 1,1-dimethylethyl, butyl and 3-methylbutyl group.

$C_1$–$C_5$ haloalkyl groups represented by Y: $C_1$–$C_5$ alkyl groups whose one or more of the hydrogen atoms are substituted with halogen atom, such as trifluoromethyl group.

Y may be phenyl, cyano or nitro group.

The integer n is preferably in the range 0 to 3.

The definitions of the corresponding substituents of the cyclopentanone derivatives of formula (2) or (4) are the same as the above.

The examples of the cycloalkanone derivatives of formula (2) or (4) usable in the present invention are listed as follows:

1-(4-chlorobenzyl)-3-methyl-2-oxocyclopentanecarboxylic acid methyl ester 1-(4-chlorobenzyl)-3-methyl-2-oxocyclopentanecarboxylic acid 1-methylethyl ester 1-(4-chlorobenzyl)-2-oxocyclopentanecarboxylic acid methyl ester 1-(4-chlorobenzyl)-2-oxocyclopentanecarboxylic acid 1-methylethyl ester 1-(4-cyanobenzyl)-3-methyl-2-oxocyclopentanecarboxylic acid methyl ester 1-(4-cyanobenzyl)-3-methyl-2-oxocyclopentanecarboxylic acid 1-methylethyl ester 1-(4-cyanobenzyl)-2-oxocyclopentanecarboxylic acid methyl ester 1-(4-cyanobenzyl)-2-oxocyclopentanecarboxylic acid 1-methylethyl ester 1-(4-nitrobenzyl)-3-methyl-2-oxocyclopentanecarboxylic acid methyl ester 1-(4-nitrobenzyl)-3-methyl-2-oxocyclopentanecarboxylic acid 1-methylethyl ester 1-(4-nitrobenzyl)-2-oxocyclopentanecarboxylic acid methyl ester 1-(4-nitrobenzyl)-2-oxocyclopentanecarboxylic acid 1-methylethyl ester 1-(4-phenylbenzyl)-3-methyl-2-oxocyclopentanecarboxylic acid methyl ester 1-(4-phenylbenzyl)-3-methyl-2-oxocyclopentanecarboxylic acid 1-methylethyl ester 1-(4-phenylbenzyl)-2-oxocyclopentanecarboxylic acid methyl ester 1-(4-phenylbenzyl)-2-oxocyclopentanecarboxylic acid 1-methylethyl ester 1-(4-methylbenzyl)-3-methyl-2-oxocyclopentanecarboxylic acid methyl ester 1-(4-methylbenzyl)-3-methyl-2-oxocyclopentanecarboxylic acid 1-methylethyl ester 1-(4-methylbenzyl)-2-oxocyclopentanecarboxylic acid methyl ester 1-(4-methylbenzyl)-2-oxocyclopentanecarboxylic acid 1-methylethyl ester 1-[4-(1,1-dimethylethyl)benzyl]-3-methyl-2-oxocyclopentanecarboxylic acid methyl ester 1-[4-(1,1-dimethylethyl)benzyl]-3-methyl-2-oxocyclopentanecarboxylic acid 1-methylethyl ester 1-[4-(1,1-dimethylethyl)benzyl]-2-oxocyclopentanecarboxylic acid methyl ester 1-[4-(1,1-dimethylethyl)benzyl]-2-oxocyclopentanecarboxylic acid 1-methylethyl ester 1-(4-chlorobenzyl)-3-ethyl-2-oxocyclopentanecarboxylic acid methyl ester 1-(4-chlorobenzyl)-3-ethyl-2-oxocyclopentanecarboxylic acid 1-methylethyl ester 1-(4-chlorobenzyl)-3-(1-methylethyl)-2-oxocyclopentanecarboxylic acid methyl ester 1-(4-chlorobenzyl)-3-(1-methylethyl)-2-oxocyclopentanecarboxylic acid 1-methylethyl ester.

For the molecular sieves used in the present invention, commercial molecular sieves are available. The pore size of the molecular sieves used in the present invention is 3, 4 or 5 angstroms preferably, particularly 3 angstroms more preferably. For the shape of the molecular sieves, the powdery shape is preferred for use in the present invention.

Such molecular sieves are used in an amount of 100 to 800 g, preferably 200 to 400 g based on one mole of the electrophilically substituted hydrogen atoms.

"One mole of hydrogen atoms" signifies that the hydrogen atoms exist by an equal number to the Avogadro's number (see Encyclopedia Chimica Vol. 9, p. 299, 1984, Kyoritsu Shuppan, Tokyo).

Preferred examples of the alkaline metal hydroxides usable in the present invention are sodium hydroxide and potassium hydroxide. The shape of such hydroxides is preferably powdery.

The amount of the alkaline metal hydroxide used in the present invention is 1 to 20 moles, preferably 4 to 10 moles based on one mole the electrophilically substituted hydrogen atoms.

Examples of alkyl halides of formula (3) or (6) are methyl bromide, methyl iodide, propyl bromide, isopropyl iodide [=(1-methylethyl) iodide], (3-methylpropyl) chloride, butyl chloride, pentyl chloride and the like.

The amount of alkyl halide used in the present invention is 0.8 to 2 moles, preferably 1 to 2 moles, more preferably 1 to 1.5 moles based on one mole of the electrophilically substituted hydrogen atoms. When the used alkyl halide is not alkyl iodide, it is preferable to add a catalytic amount, usually 0.5 to 10 mol %, of an alkaline metal iodide to the reaction mixture.

The reactions in the present invention are carried out in a solvent or a mixed solvent. Preferred examples of the organic solvents usable in the present invention are listed as follows:

Aromatic hydrocarbons: benzene, toluene, xylene, methylnaphthalene, etc.

Aliphatic hydrocarbons: pentane, hexane, heptane, cyclohexane, ethylcyclohexane, etc.

Amide-type solvents: N,N-dimethylformamide, N,N-dimethylacetamide, N,N-diethylacetamide, N-methyl-2-pyrrolidone, etc.

Ethers: diethyl ether, dimethoxyethane, diisopropyl ether, tetrahydrofuran, dioxane, etc.

Sulfur-containing compounds: dimethyl sulfoxide, tetramethylene sulfone, etc.

The reaction temperature is −20° to 60° C. For an operational reason, the reaction temperature may slightly higher or lower than the above range within that no adverse effect is given to the yield.

According to the present invention, there is prepared a mixture containing a cycloalkanone derivative, an alkyl halide, molecular sieves and an alkaline metal hydroxide (an alkaline metal iodide may be additionally mixed, if necessary), and the resultant mixture is stirred for about 0.5 to 24 hours to let the said substances contact each other to complete the reaction. For an operational reason, the reaction time may exceed 24 hours within that no adverse effect is given to the yield.

According to the above-described process of the present invention, an alkylcyclopentanone derivative of formula (1) or (5) can be obtained in a remarkably high yield due to the presence of both an alkaline metal hydroxide and molecular sieves in the reaction system.

EXAMPLES

The present invention is further illustrated to the examples thereof, which examples however are merely intended to be illustrative and not to be construed as limiting the scope of the invention. In the following Preparation Examples and Comparative Preparation Examples, the yield of the objective product was determined by gas chromatography.

Preparation Example 1

Preparation of 1-(4-chlorobenzyl)-3,3-dimethyl-2-oxocyclomentanecarboxylic Acid Methyl Ester In a 500-ml four-necked flask equipped with a condenser having a calcium chloride pipe, a stirrer and a thermometer, there were placed 7 g (25 mmol) of 1-(4-chlorobenzyl)-3-methyl-2-oxocyclopentanecarboxylic acid methyl ester [hereinafter referred to as starting material], 44 ml of toluene, 6 ml of N-methyl-2-pyrrolidone, 0.075 g of sodium iodide, 2.8 g of methyl bromide and 5 g of mortar-ground molecular sieves (0.3 nm beads about 2 mm, produced by Merck & Co., Ltd.), and the mixture temperature was maintained at 20° C.

To the resultant mixture, 4.75 g of mortar-ground sodium hydroxide was added and the obtained mixture was stirred vigorously and reacted for one hour.

The reaction solution was poured into ice water and extracted twice with 100 ml of toluene, and the extracts were joined, washed with water and then dried over anhydrous sodium sulfate, after which toluene was evaporated away to obtain 5.2 g of 1-(4-chlorobenzyl)-3,3-dimethyl-2-oxocyclopentanecarboxylic acid methyl ester. Yield: 71%.

There was detected no unreacted portion of starting material.

Preparation Example 2

Preparation of 1-(4-chlorobenzyl)-3,3-dimethyl-2-oxocyclopentanecarboxylic Acid 1-methylethyl Ester In a 500-ml four-necked flask equipped with a condenser having a calcium chloride pipe, a stirrer and a thermometer, there were placed 19.0 g of mortar-ground sodium hydroxide, 132 ml of toluene, 18 ml of N-methyl-2-pyrrolidone, 0.3 g of sodium iodide, 11.4 g of methyl bromide and 40 g of mortar-ground molecular sieves (0.3 nm beads about 2 mm, produced by Merck & Co., Ltd.). To the resultant mixture with vigorous stirring, 30.9 g (100 mmol) of 1-(4-chlorobenzyl)-3-methyl-2- oxocyclopentanecarboxylic acid 1-methylethyl ester [starting material] dissolved in a mixture of 6 ml of N-methyl-2-pyrrolidone and 44 ml of toluene was added dropwise at 20° C. over a period of 2 hours. The reaction was allowed to continue for 4 hours till the starting material was consumed.

The reaction solution was poured into ice water and extracted twice with 150 ml of toluene. The extracts were joined, washed with water and then dried over anhydrous sodium sulfate, after which toluene was evaporated away to obtain 28.9 g of 1-(4-chlorobenzyl)-3,3-dimethyl-2-oxocyclopentanecarboxylic acid 1-methylethyl ester. Yield: 90%.

Preparation Example 3

Preparation of 1-(4-chlorobenzyl)-3,3-dimethyl-2-oxocyclopentanecarboxylic Acid 1-methylethyl Ester In a 500-ml four-necked flask equipped with a condenser having a calcium chloride pipe, a stirrer and a thermometer, there were placed 29.5 g (100 mmol) of 1-(4-chlorobenzyl)-2-oxocyclopentanecarboxylic acid 1-methylethyl ester [starting material], 0.3 g of sodium iodide, 176 ml of toluene, 24 ml of N-methyl-2-pyrrolidone, 24.6 g of methyl bromide and 40 g of ground molecular sieves (0.3 nm beads about 2 mm, produced by Merck & Co., Ltd.), and the mixture was stirred and cooled to maintain the resultant mixture temperature at 2° C.

Then mortar-ground sodium hydroxide was added in four portions at intervals of one hour, 8 g each time, for a total amount of 32 g, and the obtained mixture was reacted for 2 hours till the starting material was consumed.

The reaction solution was poured into ice water and extracted twice with 100 ml of toluene, and the extracts were joined, washed with water and then dried over anhydrous sodium sulfate, after which toluene was evaporated away to obtain 25.1 g of 1-(4-chlorobenzyl)-3,3-dimethyl-2-oxocyclopentanecarboxytic acid 1-methylethyl ester. Yield: 75%.

Comparative Preparation Example 1

Preparation of 1-(4-chlorobenzyl)-3,3-dimethyl-2-oxocyclopentanecarboxylic Acid Methyl Ester In a 200-ml four-necked flask equipped with a condenser having a calcium chloride pipe, a stirrer and a thermometer, there were placed 7 g (25 mmol) of 1-(4-chlorobenzyl)-3-methyl-2-oxocyclopentanecarboxylic acid methyl ester [starting material], 44 ml of toluene, 6 ml of N-methyl-2-pyrrolidone, 0.075 g of sodium iodide and 2.8 g of methyl bromide, and the mixture temperature was maintained at 20° C.

To the resultant mixture, 4.75 g of mortar-ground sodium hydroxide was added and the obtained mixture was reacted for one hour under vigorous stirring.

The reaction solution was poured into ice water and extracted twice with 100 ml of toluene, and the extracts were joined, washed with water and dried over anhydrous sodium sulfate, after which toluene was evaporated away to obtain 2.7 g of 1-(4-chlorobenzyl)-3,3-dimethyl-2-oxocyclopentanecarboxylic acid methyl ester. Yield: 37%.

There was detected no unreacted portion of starting material.

Comparative Preparation Example 2

Preparation of 1-(4-Chlorobenzyl)-3,3-dimethyl-2-oxocyclopentanecarboxylic Acid 1-methylethyl Ester In a 200-ml four-necked flask equipped with a condenser having a calcium chloride pipe, a stirrer and a thermometer, there were placed 7.4 g (25 mmol) of 1-(4-chlorobenzyl)-2-oxocyclopentanecarboxylic acid 1-methylethyl ester [starting material], 44 ml of toluene, 6 ml of N-methyl-2-pyrrolidone, 0.075 g of sodium iodide and 5.6 g of methyl bromide, and the mixture was cooled to maintain the mixture temperature at 2° C.

To the resultant mixture, 10 g of mortar-ground sodium hydroxide was added and the obtained mixture was reacted for one hour under vigorous stirring.

The reaction solution was poured into ice water and extracted twice with 100 ml of toluene, and the extracts were joined, washed with water and dried over anhydrous sodium sulfate, after which toluene was evaporated away to obtain 1 g of 1-(4-chlorobenzyl)-3,3-dimethyl-2-oxocyclopentanecarboxylic acid 1-methylethyl ester. Yield: 12%.

There was detected no unreacted portion of starting material.

NMR spectral data ($CDCl_3$, δ and ppm) of the compounds obtained in Preparation Examples 1–3 and Comparative Preparation Examples 1 and 2 are shown below.

(11) 1-(4-chlorobenzyl)-3,3-dimethyl-2-oxocyclopentanecarboxylic acid methyl ester 0.72 (s, 3H), 1.05 (s, 3H), 1.37–2.40 (m, 4H), 3.13 (s, 2H), 3.70 (s, 3H), 7.07 (d, 2H, J=9 Hz), 7.27 (d, 2H, J=9 Hz).

(12) 1-(4-chlorobenzyl)-3,3-dimethyl-2-oxocyclopentanecarboxylic acid 1-methylethyl ester 0.67 (s, 3H), 1.07 (s, 3H), 1.17 (d, 3H×2, J=6 Hz), 1.35–2.50 (m, 4H), 3.07 (s, 2H), 4.95 (hept, 1H, J=6 Hz), 7.00 (d, 2H, J=8 Hz), 7.17 (d, 2H, J=8 Hz).

(13) 1-(4-chlorobenzyl) -3-methyl-2-oxocyclopentanecarboxylic acid methyl ester 0.83–1.12 (m, 3H), 1.40–2.63 (m, 5H), 3.12, 3.15 (2s, 2H), 3.70 (s, 3H), 7.07 (d, 2H, J=8 Hz), 7.27 (d, 2H, J=8 Hz).

(14) 1-(4-chlorobenzyl) -3-methyl-2-oxocyclopentanecarboxylic acid 1-methylethyl ester 0.90 (d, 3H, J=6 Hz), 1.18 (d, 3H×2, J=6 Hz), 1.50–2.53 (m, 5H), 3.07 (bs, 2H), 4.95 (hept, 1H, J=6 Hz), 6.97 (d, 2H, J=8 Hz), 7.17 (d, 2H, J=8 Hz).

(15) 1-(4-chlorobenzyl)-2-oxocyclopentanecarboxylic acid 1-methylethyl ester 1.18 (d, 3H×2, J=6 Hz), 1.50–2.60 (m, 6H), 3.07 (s, 2H), 4.93 (hept, 1H, J=6 Hz), 7.00 (d, 2H, J=8 Hz), 7.20 (d, 2H, J=8 Hz).

EFFECT OF THE INVENTION

Alkylcyclopentanone derivatives of formula (1) can be obtained in a remarkably high yield by use of an alkaline metal hydroxide and molecular sieves, simultaneously in the reaction system.

What is claimed is:

1. A process for producing an alkylcyclopentanone derivative of formula (1), which comprises reacting a cyclopentanone derivative of formula (2) and an alkyl halide of formula (3) in an organic solvent in the presence of molecular sieves and an alkaline metal hydroxide:

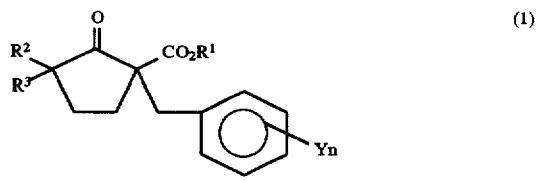

(1)

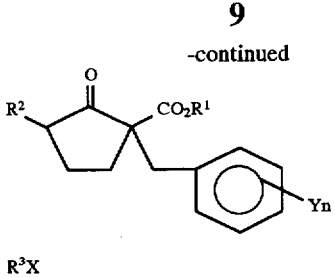

(2)

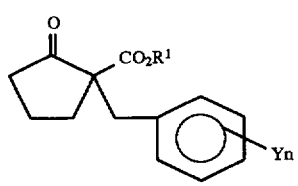

(4)

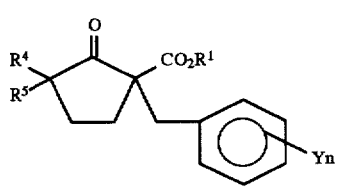

(5)

R³X (3)

wherein $R^1$ is $C_1$–$C_4$ alkyl group; $R^2$ is hydrogen atom or $C_1$–$C_5$ alkyl group; $R^3$ is $C_1$–$C_5$ alkyl group; Y is halogen atom, $C_1$–$C_5$ alkyl group, $C_1$–$C_5$ haloalkyl group, phenyl group, cyano group or nitro group; n is an integer from 0 to 5; when n is 2 or greater, Y's may be identical or different; $R^3$ in the alkyl halide is the same as $R^3$ in formula (1).

2. A process for producing an alkylcyclopentanone derivative of formula (5), which comprises reacting a cyclopentanone derivative of formula (4) and an alkyl halide of formula (6) in an organic solvent in the presence of molecular sieves and an alkaline metal hydroxide:

$R^k$X (6)

wherein $R^1$ is $C_1$–$C_4$ alkyl group; $R^4$ is $C_1$–$C_5$ alkyl group; $R^5$ is $C_1$–$C_5$ alkyl group; $R^k$ is either $R^4$ or $R^5$; Y is halogen atom, $C_1$–$C_5$ alkyl group, $C_1$–$C_5$ haloalkyl group, phenyl group, cyano group or nitro group; n is an integer of 0 to 5; when n is 2 or greater, Y's may be identical or different.

3. The process according to claim 1, wherein the organic solvent is selected from the group consisting of aromatic hydrocarbons, aliphatic hydrocarbons, amides, ethers, sulfur-containing compounds and a mixture thereof.

4. The process according to claim 2, wherein the organic solvent is selected from the group consisting of aromatic hydrocarbons, aliphatic hydrocarbons, amides, ethers, sulfur-containing compounds and a mixture thereof.

5. The process according to claim 1, wherein $R^1$ in the compounds of formulae (1) and (2) is methyl, ethyl, 1-methylethyl, propyl, 1-methylpropyl, butyl or 1,1-dimethylethyl group.

6. The process according to claim 2, wherein $R^1$ in the compounds of formulae (4) and (5) is methyl, ethyl, 1-methylethyl, propyl, 1-methylpropyl, butyl or 1,1-dimethylethyl group.

7. The process according to claim 1, wherein the alkaline metal hydroxide is sodium hydroxide or potassium hydroxide.

8. The process according to claim 2, wherein the alkaline metal hydroxide is sodium hydroxide or potassium hydroxide.

9. The process according to claim 1, wherein $R^2$ and $R^3$ in the compounds of formulae (1) and (2) are methyl, ethyl, 1-methylethyl, propyl, 2-methylpropyl, butyl, 3-methylbutyl or pentyl group.

10. The process according to claim 2, wherein $R^4$ and $R^5$ in the compound of formula (5) are methyl, ethyl, 1-methylethyl, propyl, 2-methylpropyl, butyl, 3-methylbutyl or pentyl group.

11. The process according to claim 1, wherein Y in the compounds of formulae (1) and (2) is a halogen atom which is fluorine, chlorine or bromine atom.

12. The process according to claim 2, wherein Y in the compounds of formulae (4) and (5) is a halogen atom which is fluorine, chlorine or bromine atom.

13. The process according to claim 1, wherein Y in the compounds of formulae (1) and (2) is a $C_1$–$C_5$ alkyl group which is methyl, ethyl, 1-methylethyl, propyl, 2-methylpropyl, 1,1-dimethylethyl, butyl or 3-methylbutyl group.

14. The process according to claim 2, wherein Y in the compounds of formulae (4) and (5) is a $C_1$–$C_5$ alkyl group which is methyl, ethyl, 1-methylethyl, propyl, 2-methylpropyl, 1,1-dimethylethyl, butyl or 3-methylbutyl group.

15. The process according to claim 1, wherein Y in the compounds of formulae (1) and (2) is a $C_1$–$C_5$ haloalkyl group containing trifluoromethyl group, in which one or more of hydrogen atoms are substituted with halogen atoms.

16. The process according to claim 2, wherein Y in the compounds of formulae (4) and (5) is a $C_1$–$C_5$ haloalkyl group containing trifluoromethyl group, in which one or more of hydrogen atoms are substituted with halogen atoms.

17. The process according to claim 1, wherein Y in the compounds of formulae (1) and (2) is phenyl, cyano or nitro group.

18. The process according to claim 2, wherein Y in the compounds of formulae (4) and (5) is phenyl, cyano or nitro group.

19. The process according to claim 1, wherein n in the compounds of formulae (1) and (2) is an integer of 0 to 3.

20. The process according to claim 2, wherein n in the compounds of formulae (4) and (5) is an integer of 0 to 3.

* * * * *